(12) United States Patent
Fu et al.

(10) Patent No.: US 11,312,948 B2
(45) Date of Patent: Apr. 26, 2022

(54) METHOD AND ENZYME FOR PREPARATION OF ENZYME-MODIFIED STEVIA SUGAR AND USE OF ENZYME-MODIFIED STEVIA SUGAR

(71) Applicant: BONTAC BIO-ENGINEERING (SHENZHEN) CO., LTD, Guangdong (CN)

(72) Inventors: Rongzhao Fu, Guangdong (CN); Lihui Liu, Guangdong (CN); Ming Jiang, Guangdong (CN); Yufeng Liu, Guangdong (CN); Wenshan Liu, Guangdong (CN); Xiaochun Chen, Guangdong (CN)

(73) Assignee: BONTAC BIO-ENGINEERING (SHENZHEN) CO., LTD, Guangdong (CN)

( * ) Notice: Subject to any disclaimer, the term of this patent is extended or adjusted under 35 U.S.C. 154(b) by 334 days.

(21) Appl. No.: 16/605,993

(22) PCT Filed: May 25, 2018

(86) PCT No.: PCT/CN2018/088358
§ 371 (c)(1),
(2) Date: Oct. 17, 2019

(87) PCT Pub. No.: WO2019/100676
PCT Pub. Date: May 31, 2019

(65) Prior Publication Data
US 2020/0140836 A1    May 7, 2020

(51) Int. Cl.
*C12N 9/24* (2006.01)
*C12P 19/56* (2006.01)
*C12P 19/14* (2006.01)

(52) U.S. Cl.
CPC ............ *C12N 9/2402* (2013.01); *C12P 19/14* (2013.01); *C12P 19/56* (2013.01); *C12Y 302/0108* (2013.01); *A23V 2250/258* (2013.01); *A23V 2250/262* (2013.01); *A23V 2300/36* (2013.01)

(58) Field of Classification Search
CPC ........ A23V 2250/262; A23V 2250/258; A23V 2300/36; C12P 19/14; C12P 19/56; C07H 15/256; C07H 1/00; C12N 9/2402
See application file for complete search history.

(56) References Cited

FOREIGN PATENT DOCUMENTS

WO    2015171555 A1    11/2015
WO    2016144175 A1    9/2016

OTHER PUBLICATIONS

Wang ("Beta-Fructofuranosidase [Aspergillus japonicas]", GenBank ABD97344.1, Submitted on Mar. 9, 2006, access via BLASTx search) (Year: 2006).*
International Search Report (English and Chinese) and Written Opinion issued in PCT/CN2018/088358, dated Mar. 4, 2019, 10 pages provided.
Xu et al., "Optimization of Enzymatic Modification of Steviosides", Modern Food Science and Technology, vol. 24, No. 11, 2008, with English translation of the Abstract; 4 pages provided (Cited in ISR).

* cited by examiner

*Primary Examiner* — Robert J Yamasaki
*Assistant Examiner* — Charles Zoltan Constantine
(74) *Attorney, Agent, or Firm* — Hamre, Schumann, Mueller & Larson, P C.

(57) ABSTRACT

The present invention provides a method for preparation of an enzyme-modified stevia sugar. The method includes the steps of adding a β-fructosidase to a solution in which a stevia sugar raw material and sucrose are dissolved to obtain a reaction solution, adjusting the pH of the reaction solution to be 5.0-8.0, maintaining a reaction temperature at 20-45° C., and after a reaction with stirring, collecting the enzyme-modified stevia sugar. The stevia sugar raw material includes one or more of stevioside and rebaudioside A, and the β-fructosidase is derived from *Microbacterium saccharophilum* or *Aspergillus japonicus*. The preparation method takes a short time, is efficient and convenient to operate, low in cost, high in conversion rate, green and environmentally friendly, and can be widely applied to industrial scale production. The present invention further provides an enzyme for preparation of the enzyme-modified stevia sugar and application thereof.

8 Claims, 2 Drawing Sheets
Specification includes a Sequence Listing.

METHOD AND ENZYME FOR PREPARATION OF ENZYME-MODIFIED STEVIA SUGAR AND USE OF ENZYME-MODIFIED STEVIA SUGAR

CROSS-REFERENCE TO RELATED APPLICATIONS

This application is the national stage of International Application No. PCT/CN2018/088358 filed May 25, 2018, the entire contents of which are incorporated herein by reference.

TECHNICAL FIELD

The present invention relates to the technical field of biomedicine, in particular to a method and enzyme for preparation of an enzyme-modified stevia sugar, and use of the enzyme-modified stevia sugar.

BACKGROUND OF INVENTION

Stevia sugar is 200-350 times sweeter than sucrose, has no toxic and side effects and is safe to eat. Studies have shown that stevia sugar can be used for preventing diseases such as high blood pressure, diabetes, obesity, heart diseases and dental caries, and is an ideal sweetener that can replace sucrose. Stevia sugar is the third natural sucrose substitute with development value and health promotion effects besides sugarcane and beet sugar, and is internationally known as "the world's third sucrose".

Stevia sugar is a mixture of diterpenoid glycosides containing a variety of ingredients extracted from leaves of the compositae herb, *Stevia rebaudiana*. Stevioside (St), rebaudioside A (RA) and rebaudioside C (RC) are higher in content, accounting for 90% or more in total. Natural stevia sugar is not sweet and has a bitter taste due to its own structure, aglycone steviol, which has an unpleasant aftertaste, so that the taste of stevia sugar is seriously affected and the wider industrial application is limited. Therefore, it is important to improve the sweetness characteristics of stevia sugar.

At present, it has been reported that some new sugar molecules are introduced into the stevia sugar components by enzyme or fermentation methods, the sweetness characteristics of an obtained derivative (or enzyme-modified stevia sugar) are greatly improved, and the delayed bitterness is weakened. Most of these production methods consume high energy, take a long time, and have low purity and yield. Therefore, it is necessary to develop a method for preparation of the enzyme-modified stevia sugar, wherein the method is simple in process, takes a short time, and is low in cost, high in yield and environmentally friendly.

SUMMARY OF THE INVENTION

In order to solve the above technical problems, the present invention provides a method and enzyme for preparation of an enzyme-modified stevia sugar, and application of the enzyme-modified stevia sugar; the preparation method of the present invention is simple in process, takes a short time, and is high in yield, green and safe.

The present invention provides the method for preparation of the enzyme-modified stevia sugar, and the preparation method includes the following steps of:

adding β-fructosidase (FFase) into a solution in which a stevia sugar raw material and sucrose are dissolved to obtain a reaction solution, adjusting the pH of the reaction solution to be 5.0-8.0, maintaining a reaction temperature at 20-45° C., and after a reaction with stirring, collecting the enzyme-modified stevia sugar, wherein the stevia sugar raw material includes one or more of stevioside and rebaudioside A, and the β-fructosidase is derived from *Microbacterium saccharophilum* or *Aspergillus japonicus*.

In the present invention, the stevioside (St) has a molecular formula of $C_{38}H_{60}O_{18}$, and the chemical structure is as shown in the formula I. The rebaudioside A (RA) has a molecular formula of $C_{44}H_{70}O_{23}$, and the chemical structure is as shown in the formula I.

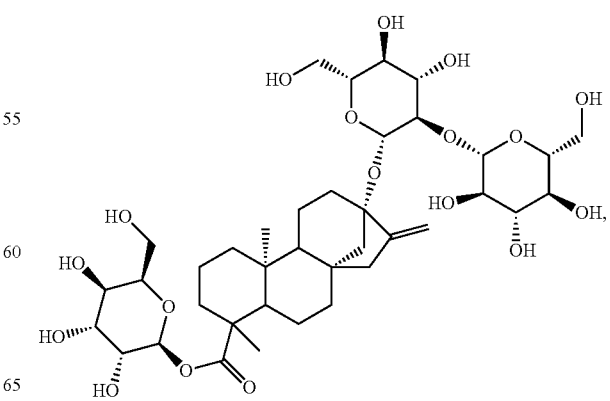

-continued

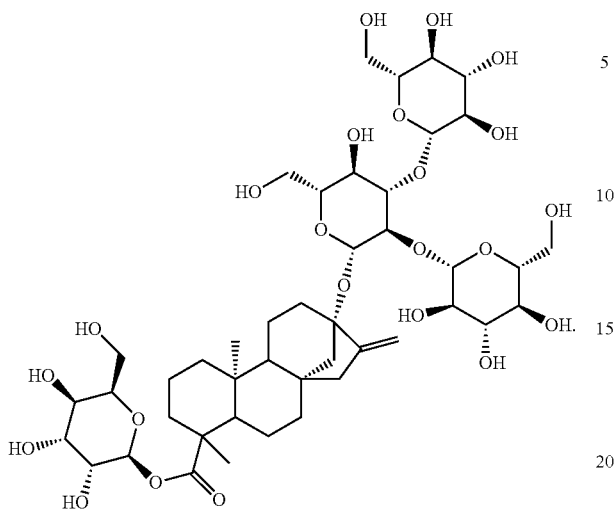

II

A specific process route of the method for preparation of the enzyme-modified stevia sugar is as shown in the formula (1):

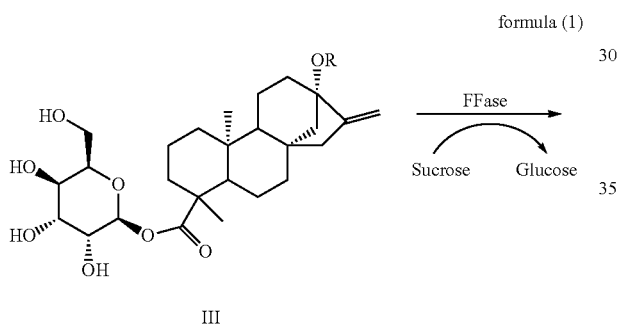

formula (1)

III

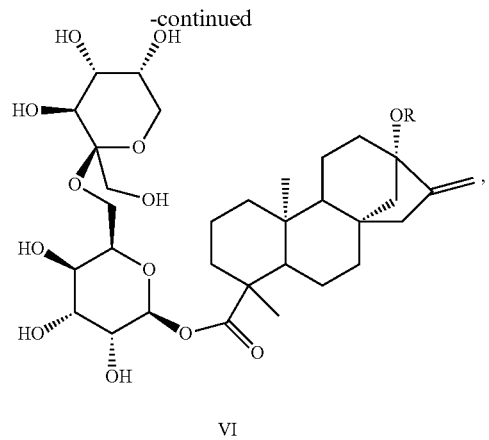

VI wherein the process adopts a biological enzyme method, and a general formula of a chemical structure of the stevia sugar raw material is as shown in the formula III, and a general formula of a chemical structure of the enzyme-modified stevia sugar is as shown in the formula IV, wherein the R groups include a disaccharide group and a trisaccharide group. The disaccharide group can be β-glc-β-glc- and the trisaccharide group can be (β-glc)$_2$-β-glc-, and the glc is glucose. The sucrose is decomposed under the catalytic action of β-fructosidase (FFase) to obtain glucose and fructose (F), wherein fructose (F) molecules are ligated to 6-OH of 19-O-β-glucosyl by β-2,6 glycosidic bonds under the catalytic action of the β-fructosidase.

In the present invention, when the stevia sugar raw material is stevioside (St), the specific process route of the method for preparation of the enzyme-modified stevia sugar is as shown in the formula (2):

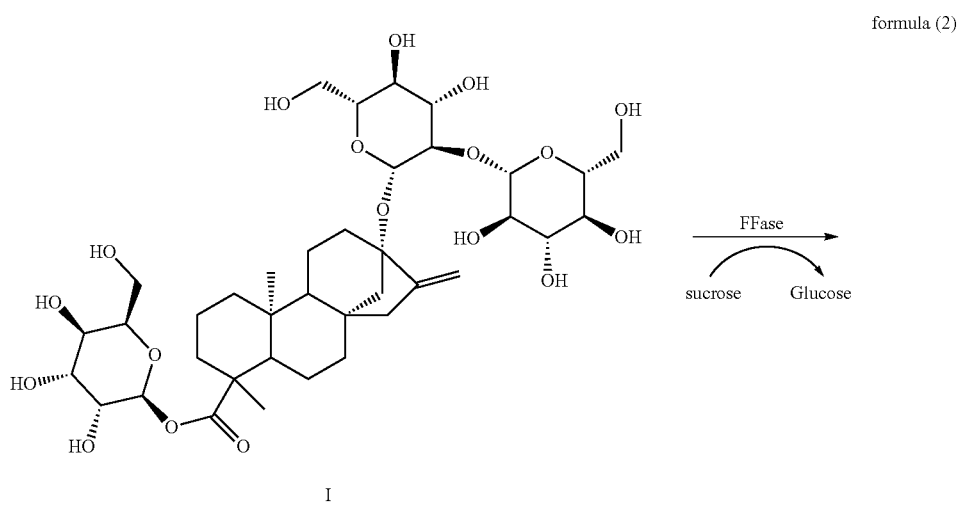

formula (2)

I

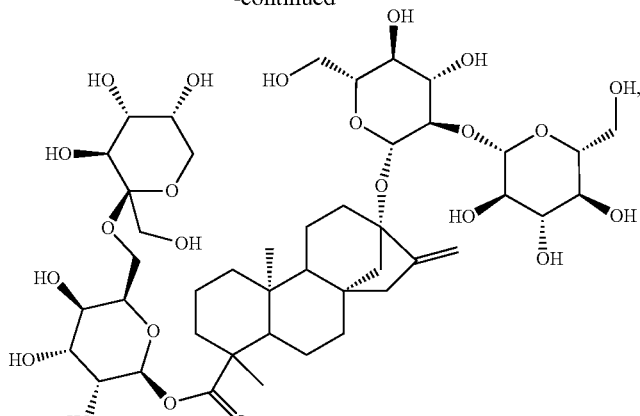

V wherein the fructose (F) molecules are ligated to 6-OH of the 19-O-β-glucosyl of stevioside the β-2,6 glycosidic bonds under the catalytic action of the β-fructosidase to obtain a stevioside derivative (St-F) as shown in the formula V. The reaction process further includes the steps of catalyzing the hydrolysis of sucrose by the β-fructosidase and obtaining glucose.

In the present invention, when the stevia sugar raw material is rebaudioside A (RA), the specific process route of the method for preparation of the enzyme-modified stevia sugar is as shown in the formula (3):

formula (3)

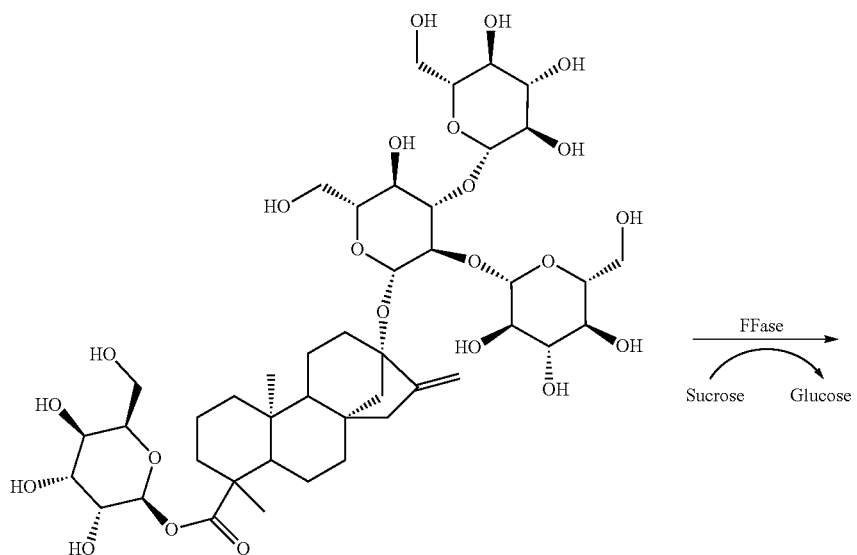

II

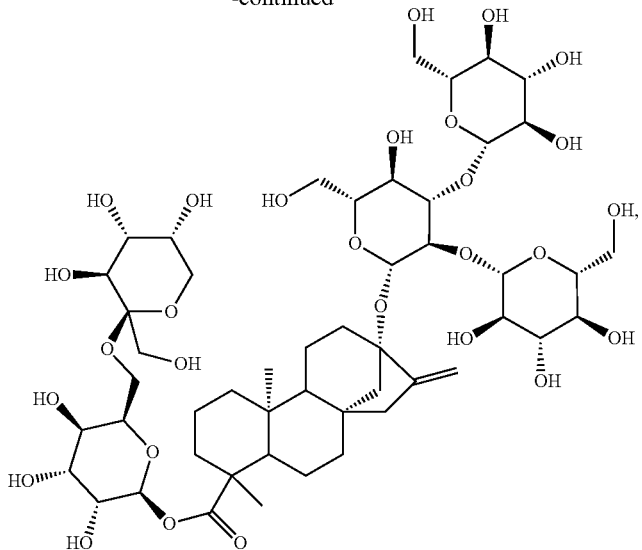

VI wherein fructose (F) molecules are ligated to 6-OH of the 19-O-β-glucosyl of rebaudioside A by the β-2,6 glycosidic bonds under the catalytic action of the β-fructosidase to obtain a rebaudioside A derivative (RA-F) as shown in the formula V. The reaction process further includes the steps of catalyzing the hydrolysis of sucrose by the β-fructosidase and obtaining glucose. The enzyme-modified stevia sugar can include one or more of enzyme-modified stevioside and enzyme-modified rebaudioside A. Preferably, the enzyme-modified stevia sugar includes one or more of stevioside derivative (St-F) and rebaudioside A derivative (RA-F).

Glycosyl groups ligated to the 19th-site of stevioside are closely related to bitterness, while stevioside 13-glycosyl groups are related to sweetness. According to the preparation method of the present invention, the stevia sugar raw material can be quickly and efficiently modified by the β-fructosidase to improve the delayed bitterness of stevia sugar, fructose groups are introduced into 6-OH of 19-O-β-glucosyl of the stevia sugar raw material (such as St or RA), and thus the sweetness of the obtained enzyme-modified stevia sugar (such as St-F or RA-F) is greatly improved.

β-fructosidase may include a first β-fructosidase or a second β-fructosidase; the gene coding sequence of the first β-fructosidase includes a nucleotide sequence as shown in SEQ ID NO: 1, and the gene coding sequence of the second β-fructosidase includes a nucleotide sequence shown in SEQ ID NO: 2.

β-fructosidase can be generated by microbial expression, wherein microbes include one or more of *Escherichia coli*, *Pichia pastoris*, and *Bacillus subtilis*. Preferably, β-fructosidase is generated by expression of *Escherichia coli*. The β-fructosidase is heterologously expressed in the system in which the β-fructosidase is generated by expression of *Escherichia coli*. According to the method, an *Escherichia coli* expression system is preferred due to simplicity, feasibility, short culture period, low fermentation cost and high enzyme yield The β-fructosidase of the present invention can be added into a reaction system in the form of lyophilized powder or a crude enzyme solution.

In the preparation method of the present invention, the pH of the reaction solution can be adjusted to be 5.0-8.0.

Preferably the pH of the reaction solution is 7.0-8.0. Particularly preferably, the pH of the reaction solution is 7.2-8.0. In the present invention, the pH of the reaction solution may be alkaline, which helps to increase the reactivity of β-fructosidase, increase the yield of the enzyme-modified stevia sugar, and shorten the reaction time.

The reaction temperature of the reaction solution can be maintained at 20-45° C. Preferably, the pH of the reaction solution is maintained at 20-30° C. Particularly preferably, the pH of the reaction solution is maintained at 20-28° C. For example, the reaction temperature of the reaction solution can be maintained at 20° C., or 25° C., or 28° C., or 35° C.

The reaction time of the reaction with stirring can be 2-5 hours, preferably 2-4 hours. In the present invention, the preparation method takes a short time, and the preferred reaction time is adopted. When the reaction time is prolonged, the conversion rate of the obtained product is lowered.

The reaction with stirring can be performed at a stirring speed of 200-300 rpm.

The process of collecting the enzyme-modified stevia sugar can include the steps of heating the reaction solution to denature β-fructosidase, filtering, collecting filtrate, and purifying the filtrate to obtain the enzyme-modified stevia sugar, wherein the heating temperature is 85-100° C. and the heating time is 0.3-1 hour; preferably, the heating temperature is 90-100° C. and the heating time is 0.5-1 hour.

The mass fraction of the stevia sugar raw material in the reaction solution may be 1%-20%. Preferably, the mass fraction of the stevia sugar raw material in the reaction solution is 10%-20%. For example, the mass fraction of the stevia sugar raw material in the reaction solution can be 10%, or 12%, or 15%, or 20%.

The mass ratio of the stevia sugar raw material to β-fructosidase can be 1:(0.1-2). Preferably, the mass ratio of the stevia sugar raw material to the β-fructosidase is 1:(0.5-2).

The mass ratio of the stevia sugar raw material to sucrose can be 1:(1-10). Preferably, the mass ratio of the stevia sugar raw material to sucrose is 1:(2-5).

The reaction solution can further include a buffer solution including any one or more of a phosphate buffer solution and a Tris-HCl buffer solution. Preferably, the buffer solution further includes other kinds of buffer solutions. Particular preferably, the buffer solution includes a sodium phosphate buffer solution. The concentration of the buffer solution can be 10-1000 mmol/L. Preferably, the concentration of the buffer solution is 10-1000 mmol/L. Particularly preferably, the concentration of the buffer solution is 100-500 mmol/L. For example, the concentration of the buffer solution can be 100 mmol/L, or 200 mmol/L, or 500 mmol/L.

β-fructosidase from different microbial species are different in enzymatic properties such as the specific activity of enzymes, the substrate range of the enzymes, the optimum pH, the optimum temperature, the action time, the stability of the enzymes. In the present invention, the β-fructosidase includes the first β-fructosidase or the second β-fructosidase, wherein the first β-fructosidase is derived from *Microbacterium saccharophilum*, and the second β-fructosidase is derived from *Aspergillus japonicus*. The β-fructosidase has hydrolase properties, can hydrolyze fructose molecules in sucrose, and has a reverse catalyzing function. Through the β-fructosidase, the fructose molecules can be ligated to 6-OH of 19-O-β-glucosyl of the stevioside and the rebaudioside A.

In the present invention, the provided preparation method takes a short time and is simple in process, low in cost, green and environmentally friendly. The prepared enzyme-modified stevia sugar has extremely high yield. Based on the same feeding ratios of the reaction substrates (the stevia sugar raw material) to the enzymes, the prior art only permits an enzyme-catalyzed reaction with a few thousands of the reaction substrate in concentration, the general conversion rate is only 40-50%, and only when the substrate concentration is close to the lowest value can the conversion rate reach about 60%, or the conversion rate can be improved by adding the raw material; while the preparation method in the present invention can permit a relatively high substrate concentration (such as 5%-20%), and the conversion rate can reach about 90%. Therefore, the preparation cost is low and the industrial production is facilitated.

The present invention further provides the enzyme for preparation of the enzyme-modified stevia sugar. The enzyme for preparation includes the β-fructosidase comprising the first β-fructosidase or the second β-fructosidase; the gene coding sequence of the first β-fructosidase includes thenucleotide sequence as shown in SEQ ID NO: 1, and the gene coding sequence of the second β-fructosidase includes the nucleotide sequence shown in SEQ ID NO: 2. The first β-fructosidase is derived from *Microbacterium saccharophilum*, and the second β-fructosidase is derived from *Aspergillus japonicus*.

The amino acid sequence of the first β-fructosidase may include an amino acid sequence as shown in SEQ ID NO: 3. The amino acid sequence of the second β-fructosidase may include an amino acid sequence as shown in SEQ ID NO: 4.

The gene coding sequence of the amino acid sequence shown in SEQ ID NO: 3 is as shown in SEQ ID NO: 1; the gene coding sequence of the amino acid sequence of the first β-fructosidase should take degenerate bases into consideration; that is, the coding gene of the amino acid sequence shown in SEQ ID NO: 3 includes nucleotide sequences shown in SEQ ID NO: 1, the nucleotide sequences having the base degenerate properties as shown in SEQ ID NO: 1 should be in the protection scope, and the amino acid sequences corresponding to these nucleotide sequences are still as shown in SEQ ID NO: 3. Similarly, the coding gene of the amino acid sequence, shown in SEQ ID NO: 4, of the second β-fructosidase should also consider degenerate bases.

The β-fructosidase may be expressed in the microbes by constructing recombinant plasmids, and carrier vectors of the recombinant plasmids may be pET28a(+) carrier vectors. The gene coding sequences of the first β-fructosidase and/or the second β-fructosidase are inserted into the pET28a(+) carrier vectors to obtain the recombinant plasmids. The recombinant plasmids can be efficiently heterologously expressed with a high yield in microbial cells to obtain the first β-fructosidase and/or the second β-fructosidase.

The nucleotide sequence of a His-tag (histidine tag) is added to the gene coding sequences of the first β-fructosidase and/or the second β-fructosidase to enable expressed protein to carry the His tag. The His tag is beneficial to separation and purification of the expressed protein, as well as analysis and tracking in experiments, such as analysis used for immunoblot experiments.

In the present invention, the provided enzyme (β-fructosidase) for preparation of the enzyme-modified stevia sugar has good biological activity and high purity, and can be widely used in the fields of food sweetener preparation, biological pharmacy and the like. Compared with other conventional fermentation systems, the preferred β-fructosidase of the present invention has higher yield, takes a shorter time, and has greater biological activity and specificity.

Furthermore, the present invention provides application of the β-fructosidase or microbial strains containing β-fructosidase genes for catalysis, wherein the β-fructosidase is encoded by the β-fructosidase genes derived from *Microbacterium saccharophilum* or *Aspergillus japonicus*. The β-fructosidase catalyzes the conversion of a compound shown in the formula III into a compound shown in the formula IV,

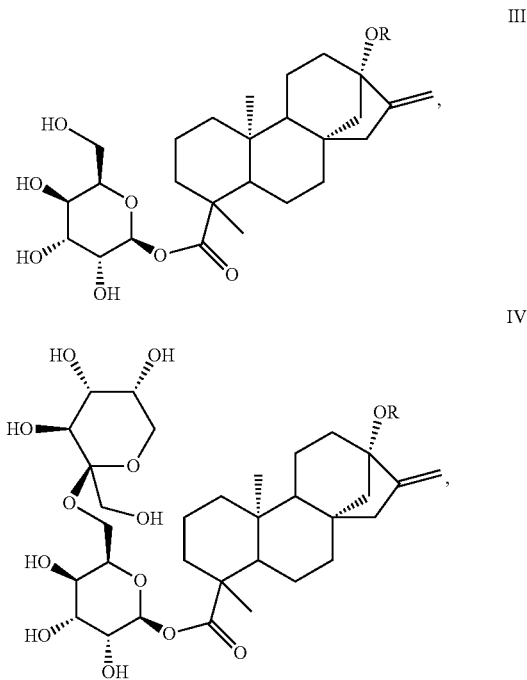

wherein the R group is β-glc-β-glc-, (β-glc)₂-β-glc-, (β-glc, α-rha-)-β-glc-, α-rha-β-glc-, β-glc-, (β-glc, β-xyl)-β-glc- or H, the glc is glucose, the rha is rhamnose, and the xyl is xylose. The process that the β-fructosidase catalyzes conversion of the compound shown in the formula III into the compound shown in the formula IV further includes the step of catalytically hydrolyzing sucrose for conversion into glucose.

When the R group is β-glc-β-glc-, the compound shown in the formula III is stevioside; when the R group is (β-glc)$_2$-β-glc-, the compound shown in the formula III is rebaudioside A; when the R group is (β-glc, α-rha-)-β-glc-, the compound shown in the formula III is rebaudioside C; when the R group is α-rha-β-glc-, the compound shown in the formula III is dulcoside A; when the R group is β-glc-, the compound shown in the formula III is rubusoside; and when the R group is (β-glc, β-xyl)-β-glc-, the compound shown bin the formula IV is rebaudioside F. Specifically, the β-fructosidase can make the fructosyl groups connected to 6-OH of 19-O-β-glucosyl of the compound shown in the formula III by the β-2, 6 glycosidic bonds to obtain a compound shown in the formula IV. For example, the β-fructosidase can make fructosyl groups to 6-OH of 19-O-β-glucosyl of the stevioside by β-2, 6 glycosidic bonds to obtain a stevioside derivative, or make fructosyl groups to 6-OH of 19-O-β-glucosyl of the stevioside by the β-2, 6 glycosidic bonds to obtain a rebaudioside A derivative and the like.

Preferably, the β-fructosidase has an amino acid sequence as shown in SEQ ID NO: 3 or SEQ ID NO: 4. The gene coding sequence of β-fructosidase includes the nucleotide sequence as shown in SEQ ID NO: 1 or SEQ ID NO: 2. The present invention further provides the recombinant plasmids. The recombinant plasmids include the gene coding sequence of the first β-fructosidase or the second β-fructosidase, wherein the gene coding sequence of the first β-fructosidase includes the nucleotide sequence as shown in SEQ ID NO: 1, and the gene coding sequence of the second β-fructosidase gene coding sequence includes the nucleotide sequence as shown in SEQ ID NO: 2.

Preferably, the gene coding sequence of the first β-fructosidase or the second β-fructosidase is inserted between BamH I and Hind III digestion sites of the pET28a(+) carrier vectors. When the gene coding sequence of the first β-fructosidase or the second β-fructosidase is inserted in the pET28a(+) carrier vectors, a start codon (such as ATG) can be added in the 5' end of the gene coding sequence of the first β-fructosidase or the second β-fructosidase gene coding sequence to be connected to the BamHI digestion sites in the pET28a(+) carrier vectors, and a stop codon (such as TAA) can be added in the 3' end of the gene coding sequence to be connected to the Hind III digestion sites in the pET28a(+) carrier vectors.

The present invention further provides a method for preparing the recombinant plasmids, and the method includes the following steps of:

1. providing an upstream primer and a downstream primer, wherein base sequences of the upstream primer and the downstream primer being are as shown in SEQ ID NO: 5-SEQ ID NO: 8 respectively;

2. providing or preparing a genetic template of the first β-fructosidase or the second β-fructosidase, and amplifying the gene segments of the first β-fructosidase or the second β-fructosidase by using the upstream primer and the downstream primer in the step (1) as PCR primers;

and 3. taking the pET28a(+) carrier vectors, performing double digestion reactions on the gene segments of the first β-fructosidase or the second β-fructosidase obtained by amplification in the step 2 and the pET28a(+) carrier vectors by using the same endonuclease respectively, performing connection after purification and recovery and obtaining the recombinant plasmids.

wherein the digestion sites for the double digestion reactions can be BamH I and Hind III endonuclease.

The advantages of the present invention are as follows:

1. The preparation method adopts the biological enzyme method, takes a short time, is simple and convenient to operate, high in conversion rate, green and safe, and can be widely applied to industrial scale production.

2. according to the preparation method, the final concentration of the substrate can reach 1%-20%, which is much higher than that of a substrate in a conventional process.

3. the prepared enzyme-modified stevia sugar has stable properties, high sweetness, greatly improved delayed bitterness and low calorific value, and can be widely applied in the food industry and pharmaceutical fields.

4. the prepared enzyme-β-fructosidase has good biological activity and high specificity.

DESCRIPTION OF EMBODIMENTS

The following are preferred execution modes of the present invention, and it should be noted that those with ordinary skills in the art can make some modifications and additions without departing from the principles of the embodiments of the present invention. These modifications and additions are also considered to fall within the protection scope of the embodiments of the present invention.

Unless otherwise stated, raw materials and other chemical reagents used in the embodiments of the present invention are all commercially available.

(1). Construction of the Recombinant Plasmids pET28a-FFase01 and pET28a-FFase02

Step a), the upstream primer and the downstream primer are provided, and the gene coding sequence of the β-fructosidase is obtained through experiments. The β-fructosidase (FFase) includes the first β-fructosidase (FFase01) or the second β-fructosidase (FFase02). The gene coding sequence of the first β-fructosidase includes the nucleotide sequence as shown in SEQ ID NO: 1, and the first β-fructosidase is derived from *Microbacterium saccharophilum*; the gene coding sequence of the second i-fructosidase gene coding sequence includes the nucleotide sequence shown in SEQ ID NO: 2, and the second i-fructosidase is derived from *Aspergillus japonicus*. The base sequence of the upstream primer corresponding to the first i-fructosidase is shown in SEQ ID NO: 5, and the base sequence of the downstream primer is shown in SEQ ID NO: 6. The base sequence of the upstream primer corresponding to the second i-fructosidase is shown in SEQ ID NO: 7, and the base sequence of the downstream primer is shown in SEQ ID NO: 8.

Figure 1:
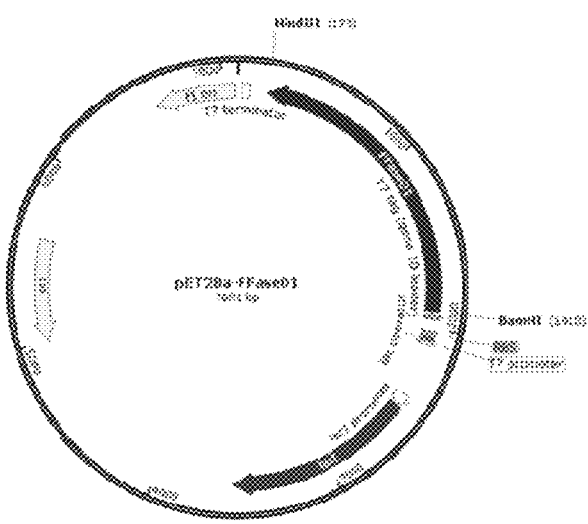
FIG. 1 is a plasmid profile of the recombinant plasmid pET28a-FFase01 according to one embodiment of the present invention.
Figure 2:
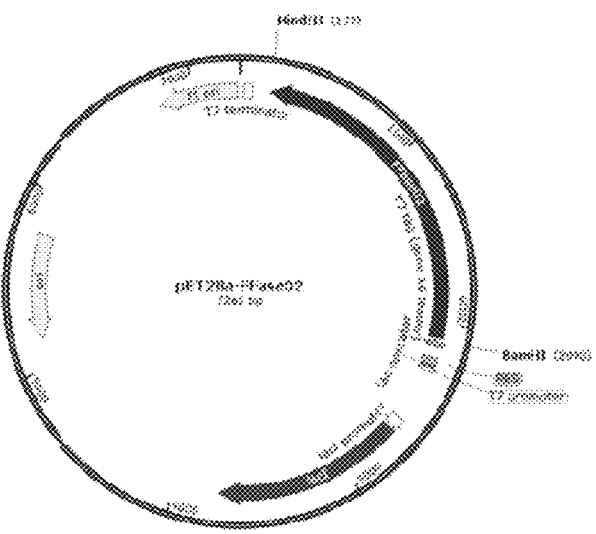
FIG. 2 is a plasmid profile of the recombinant plasmid pET28a-FFase02 according to an embodiment of the present invention.

Step b), the gene coding sequence of the FFase01 or the FFase02 is inserted between BamH I and Hind III digestion sites of the pET28a(+) carrier vectors. When the gene coding sequence of the FFase01 or the FFase02 is inserted into the pET28a(+) carrier vectors, the start codon (such as ATG) is added in the 5' end of the gene coding sequence of the FFase01 or the FFase02 to be connected to the BamHI digestion sites in the pET28a(+) carrier vectors, and the stop codon (such as TAA) is further added in the 3' end to be connected to the Hind III digestion sites in the pET28a(+) carrier vectors. Then, the carrier vectors are transferred into *Escherichia coli* competent cells DH5a, and positive clone PCR identification and sequencing identification are performed. After PCR product gel electrophoresis detection and sequencing identification, target fragments with the required size and sequences are obtained, and the recombinant plasmids pET28a-FFase01 or pET28a-FFase02 are successfully constructed. FIGS. 1 and 2 show profiles of the recombinant plasmids pET28a-FFase01 or pET28a-FFase02, respectively.

Step (2). Expression of β-Fructosidase FFase01 or FFase02

One or more of the constructed recombinant plasmids pET28a-FFase01 and pET28a-FFase02 is/are transferred into *Escherichia coli* BL21 (DE3), and inoculated into 4 mL of LB medium with the inoculation amount of 1% at the constant temperature of 37° C. and the shaking speed of 200 rpm; after overnight culture, the bacterial solution is transferred into a 2 L triangular flask containing 1 L of LB medium (50 μg/mL kanamycin) with the inoculation amount of 1% for further culture at the constant temperature of 37° C., an inducer IPTG with the final concentration of 0.1 mM-1 mM is added until the OD600 value in the medium reaches about 0.6, and the culture continues at 20-37° C. for 12-16 hours and then thalli are collected by centrifugation. The thalli are resuspended in a 50 mM phosphate buffer solution (pH=7.4), sonicated and centrifuged, and supernatant is collected to obtain a crude enzyme solution containing FFase01 or FFase02.

The crude enzyme solution obtained by expression and containing FFase01 or FFase02 is identified by SDS-polyacrylamide gel electrophoresis (SDS-PAGE). In the crude enzyme solution obtained by expression in this embodiment, the molecular sizes of the FFase01 and FFase02 are similar to the theoretical calculation values of the corresponding protein, where the theoretical molecular weight of FFase01 is 64 kDa, and the theoretical molecular weight of FFase02 is 70 kDa. In addition, the collected crude enzyme solution can be further purified to obtain lyophilized powder of FFase01 or FFase02.

Step (3). Comparison of Catalytic Activities of FFase01 or FFase02

In the operation processes of the above steps (1) and (2), β-fructosidases FFase03-FFase05 from other sources are obtained; wherein the β-fructosidase FFase03 is derived from *Schwanniomyces occidentalis*, the β-fructosidase FFase04 is derived from *Lactobacillus crispatus*, and the β-fructosidase FFase05 is derived from *Cichorium intybus*. A reaction system is designed: 5 mg of stevioside or rebaudioside A is added into 1 mL of sodium phosphate buffer solution, 20 mg of sucrose is added, and stirring is performed for complete dissolution; 200 μL (50 mg) of crude enzyme solution of any one of β-fructosidases FFase01-FFase05 is added, and the pH is adjusted to 7.4; the reaction occurs at the temperature of 20° C. and the stirring speed of 200 rpm for 5 hours, the enzyme-modified stevioside is collected, and the enzyme activities of each kind of β-fructosidase can be evaluated and seen in the following table:

| Enzyme name | Enzyme source | Conversion rate | Enzyme activity |
|---|---|---|---|
| FFase01 | *Microbacterium saccharophilum* | 92% | Effective |
| FFase02 | *Aspergillus japonicus* | 93% | Effective |
| FFase03 | *Schwanniomyces occidentalis* | Zero | Invalid |
| FFase04 | *Lactobacillus crispatus* | | Invalid |
| FFase05 | *Cichorium intybus* | | Invalid |

Embodiment 1

Figure 3:
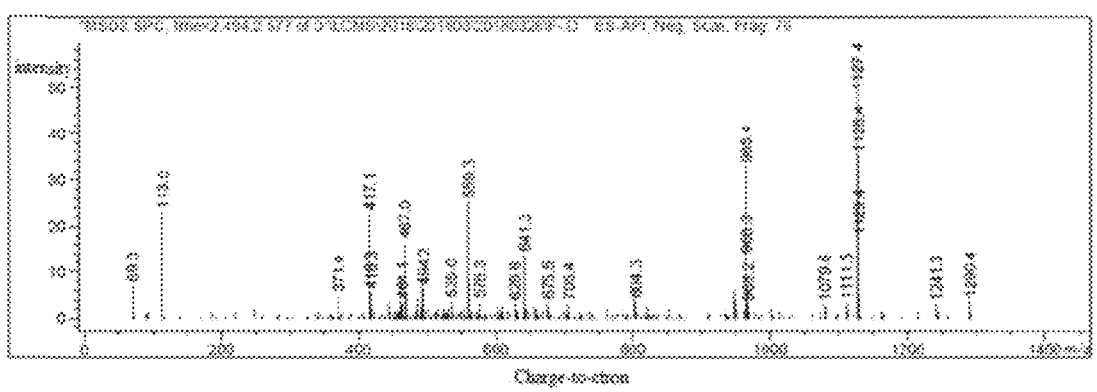
FIG. 3 is a mass spectrogram of the RA-F according to an embodiment of the present invention.

A method for preparation of an enzyme-modified stevia sugar including the following steps of:

in 500 mL of sodium phosphate buffer solution, adding 50 mg of rebaudioside A and 100 g of sucrose respectively, and stirring for complete dissolution; adding 10 g of FFase01 lyophilized enzyme powder, and adjusting the pH to 7.4; reacting at the temperature of 35° C. and the stirring speed of 250 rpm for 2 hours; after the reaction is completed, heating the reaction solution to 100° C. for heat treatment 0.5 hour so that the FFase01 protein can be denatured and removed by filtration, collecting filtrate and spray-drying the filtrate to obtain a crude enzyme-modified stevia sugar, and making the crude enzyme-modified stevia sugar subjected to separation with silicone resin, crystallization and other after-treatments and purification to obtain 51.73 g of enzyme-modified stevia sugar RA-F, wherein the purity is greater than 95%. In this embodiment, the reaction solution is extracted at a fixed time for mass spectrometry analysis; FIG. 3 is the mass spectrum of the enzyme-modified stevia sugar RA-F detected during an experiment, and according to the measurement data of the reaction solution by the liquid chromatography, calculation is performed to obtain the conversion rate of 91.5%.

Embodiment 2

Figure 4:
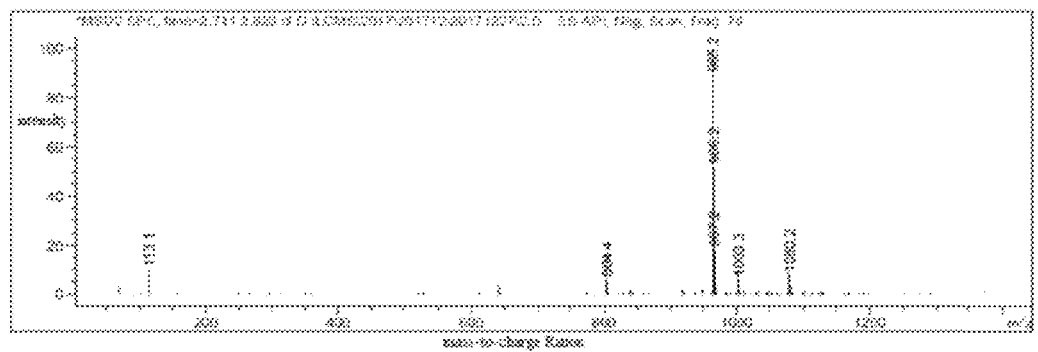
FIG. 4 is a mass spectrogram of the St-F according to an embodiment of the present invention.

A method for preparation of an enzyme-modified stevia sugar including the following steps of:

in 500 mL of sodium phosphate buffer solution, adding 50 g of stevioside and 100 g of sucrose respectively, and stirring for complete dissolution; adding 10 g of FFase01 lyophilized enzyme powder, and adjusting the pH to 7.4; reacting at the temperature of 35° C. and the stirring speed of 250 rpm for 2 hours; after the reaction is completed, heating the reaction solution to 100° C. for heat treatment 0.5 hour so that the FFase01 protein can be denatured and removed by filtration, collecting filtrate and spray-drying the filtrate to obtain a crude enzyme-modified stevia sugar, and making the crude enzyme-modified stevia sugar subjected to separation by silicone resin, crystallization and other after-treatments and purification to obtain 51.85 g of enzyme-modified stevia sugar St-F, wherein the purity is greater than 95%. In this embodiment, the reaction solution is extracted at a fixed time for mass spectrometry analysis; FIG. 4 is the mass spectrum of the enzyme-modified stevia sugar St-F detected during an experiment, and according to the measurement data of the reaction solution by the liquid chromatography, calculation is performed to obtain the conversion rate of 92.0%.

Embodiment 3

A method for preparation of an enzyme-modified stevia sugar including the following steps of:

in 500 mL of sodium phosphate buffer solution, adding 50 g of stevioside and 100 g of sucrose respectively, and stirring for complete dissolution; adding 10 g of FFase02 lyophilized enzyme powder, and adjusting the pH to 7.4; reacting at the temperature of 28° C. and the stirring speed of 250 rpm for 2 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 52.64 g of enzyme-modified stevia sugar St-F, wherein the purity is greater than 95%, and the conversion rate measured by the experiment is 92.4%.

Embodiment 4

A method for preparation of an enzyme-modified stevia sugar including the following steps of:

in 500 mL of sodium phosphate buffer solution, adding 50 g of stevioside and 200 g of sucrose respectively, and stirring for complete dissolution; adding 5 g of FFase02 lyophilized enzyme powder, and adjusting the pH to 7.4; reacting at the temperature of 28° C. and the stirring speed of 250 rpm for 2 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 53.27 g of enzyme-modified stevia sugar St-F, wherein the purity is greater than 95%, and the conversion rate measured by the experiment is 93.5%.

Embodiment 5

A method for preparation of an enzyme-modified stevia sugar including the following steps of:

in 500 mL of sodium phosphate buffer solution, adding 50 g of stevioside and 100 g of sucrose respectively, and stirring for complete dissolution; adding 5 g of FFase02 lyophilized enzyme powder, and adjusting the pH to 8.0; reacting at the temperature of 28° C. and the stirring speed of 250 rpm for 2 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 51.98 g of enzyme-modified stevia sugar St-F, wherein the purity is greater than 95%, and the conversion rate measured by the experiment is 91.3%.

Embodiment 6

A method for preparation of an enzyme-modified stevia sugar including the following steps of:

in 500 mL of sodium phosphate buffer solution, adding 50 g of stevioside and 100 g of sucrose respectively, and stirring for complete dissolution; adding 5 g of FFase02 lyophilized enzyme powder, and adjusting the pH to 7.4; reacting at the temperature of 28° C. and the stirring speed of 250 rpm for 4 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 52.72 g of enzyme-modified stevia sugar St-F, wherein the purity is greater than 95%, and the conversion rate measured by the experiment is 92.6%.

Embodiment 7

A method for preparation of an enzyme-modified stevia sugar including the following steps of:

in 500 mL of sodium phosphate buffer solution, adding 50 g of stevioside and 100 g of sucrose respectively, and stirring for complete dissolution; adding 5 g of FFase02 lyophilized enzyme powder, and adjusting the pH to 8.0; reacting at the temperature of 20° C. and the stirring speed of 250 rpm for 4 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 52.39 g of enzyme-modified stevia sugar St-F, wherein the purity is greater than 95%, and the conversion rate measured by the experiment is 92.1%.

Embodiment 8

A method for preparation of an enzyme-modified stevia sugar including the following steps of:

in 500 mL of sodium phosphate buffer solution, adding 100 g of stevioside and 200 g of sucrose respectively, and stirring for complete dissolution; adding 20 g of FFase02 lyophilized enzyme powder, and adjusting the pH to 7.4; reacting at the temperature of 28° C. and the stirring speed of 250 rpm for 2 hours; after the reaction is completed, heating the reaction solution to 100° C. for heat treatment 0.5 hour so that the FFase02 protein can be denatured and removed by filtration, collecting filtrate and spray-drying the filtrate to obtain a crude enzyme-modified stevia sugar, and making the crude enzyme-modified stevioside subjected to separation by silicone resin, crystallization and other aftertreatments and purification to obtain 107.21 g of enzyme-modified stevia sugar St-F, wherein the purity is greater than 95%, and the conversion rate measured by the experiment is 91.3%.

It is to be understood that the foregoing specific and detailed descriptions in the embodiments are merely illustrative of some modes of the invention, but are not to be construed as limiting the patent scope of the present invention. It should be noted that a number of modifications and additions may be made by those with ordinary skills in the art without departing from the conception of the present invention. These all fall within the protection scope of the present invention. Therefore, the protection scope of the present invention should be subject to the appended claims.

The invention claimed is:

1. A method for preparation of an enzyme-modified stevia sugar, comprising the steps of:

adding β-fructosidase to a solution in which a stevia sugar raw material and sucrose are dissolved to obtain a reaction solution, adjusting the pH of the reaction solution to be 5.0-8.0, maintaining a reaction temperature at 20-45° C., and after a reaction with stirring, collecting the enzyme-modified stevia sugar, wherein the stevia sugar raw material comprises one or more of stevioside and rebaudioside A, and the β-fructosidase is derived from *microbacterium saccharophilum* or *aspergillus japonicus*.

2. The preparation method according to claim 1, wherein the β-fructosidase comprises a first β-fructosidase or a second β-fructosidase; a gene coding sequence of the first β-fructosidase comprises a nucleotide sequence as shown in SEQ ID NO: 1, and a gene coding sequence of the second β-fructosidase comprises a nucleotide sequence shown in SEQ ID NO: 2.

3. The preparation method according to claim 1, wherein the reaction time of the reaction with stirring is 2-5 hours.

4. The preparation method according to claim 1, wherein the process of collecting the enzyme-modified stevia sugar comprises the steps of heating the reaction solution to denature the β-fructosidase, filtering, collecting filtrate, and purifying the filtrate to obtain the enzyme-modified stevia sugar, wherein the heating temperature is 85-100° C. and the heating time is 0.3-1 hour.

5. The preparation method according to claim 4, wherein the step of purifying the filtrate comprises: spray drying the filtrate to obtain crude enzyme-modified stevia sugar, and subjecting the crude enzyme-modified stevia sugar to separation by silicone resin and crystallization to obtain the enzyme-modified stevia sugar.

6. The preparation method according to claim 1, wherein the mass fraction of the stevia sugar raw material in the reaction solution is 1%-20%.

7. The preparation method according to claim 1, wherein the mass ratio of the stevia sugar raw material to the β-fructosidase is 1:01-2.

8. The preparation method according to claim 1, wherein the reaction solution further comprises a buffer solution selected from the group consisting of a phosphate buffer solution and a Tris-HCl buffer solution.

* * * * *

SEQUENCE LISTING

<160> NUMBER OF SEQ ID NOS: 8

<210> SEQ ID NO 1
<211> LENGTH: 1731
<212> TYPE: DNA
<213> ORGANISM: Artificial Sequence
<220> FEATURE:
<223> OTHER INFORMATION: the sequence is synthetized

<400> SEQUENCE: 1

| | |
|---|---|
| acccatagca cccgcggccg cgtgcgccgc gtgctggcgg gcggcctggc gaccagcacc | 60 |
| ctggcggcgg cggtgctgat tgcgggcgcg gcgccggcga ccgcgcagag cggcctgcag | 120 |
| gatggcccgg aaccgaccat tcatacccag caggcgtatg cgccggaaga tgattttacc | 180 |
| gcgaaatgga cccgcgcgga tgcgcgccag ctgcagcgca tgagcgatcc gaccgcgccg | 240 |
| agccgcgaaa acagcatgcc ggcgagcgtg accatgccga ccgtgccgca ggattttccg | 300 |
| gatatgagca acgaacaggt gtgggtgtgg gatacctggc cgctgaccga tgaagatgcg | 360 |
| aaccagtata gcgtgaacgg ctgggaaatt attttttagcc tggtggcgga tcgcaacctg | 420 |
| ggctttgatg atcgccatgt gtttgcgaaa attggctatt tttatcgccc ggcgggcgtg | 480 |
| ccggcggcgg aacgcccgga aaacggcggc tggacctatg cggcctggt gtttaaagaa | 540 |
| ggcgtgaccg ccagattttt tgaagatcag agctttagcc atcagaccca gtggagcggc | 600 |
| agcgcgcgcg tgagcaaaaa cggcgaaatt aaactgtttt ttaccgatgt ggcgttttat | 660 |
| cgcaacagcg atggcaccaa cattaaaccg tatgatccgc gcattgcgct gagcgtgggc | 720 |
| aaagtgaaag cgaacaaaaa aggcgtgacc ctgaccggct taacaaagt gaccgatctg | 780 |
| ctgcaggcgg atggcaccta ttatcagacc ggcgcgcaga acgaattttt taactttcgc | 840 |
| gatccgtttta cctttgaaga tccggcgcat ccgggcgaaa cctttatggt gtttgaaggc | 900 |
| aacagcgcga tgcagcgcga aaccgcgacc tgcaacgaag cggatctggg ctatcgccag | 960 |
| ggcgatccgt atgcggaaac cgtggatgat gtgaacgcga gcggcgcgac ctatcagatt | 1020 |
| ggcaacgtgg gcctggcgaa agcgaaaaac aaacagctga ccgaatggga atttctgccg | 1080 |
| ccgattctga gcgcgaactg cgtgaccgat cagaccgaac gcccgcagat ttattttaaa | 1140 |
| gatggcaaaa gctatctgtt taccattagc catcgcggca cctttgcggc gggcctggat | 1200 |
| ggcccggaag gcgtgtatgg ctttgtgggc gatggcattc gcagcgatta tcagccgctg | 1260 |
| aacggcggca gcggcctggc gctgggcaac ccgaccaacc tgaactttct gggcggccag | 1320 |
| ccgtttgcgc cggattttaa ccagcatccg ggccattttc aggcgtatag ccattatgtg | 1380 |
| atgccgggcg gcctggtgca gagctttatt gataccattg gcacccatga tgattttgtg | 1440 |
| cgcggcggca ccctggcgcc gaccgtgaaa atggatattg gcgtgggcgg cgatccgacc | 1500 |
| aaaaccgcgg tggattatag ctatggcagc gaaggcctgg gcggctgggc ggatattccg | 1560 |
| gcgaacaaac atctgtttac caacggcaaa tttggcgtgg cggtgagcga tgaagcggcg | 1620 |
| cagaaaattc gcaaaattct gggcagcaaa tttgatgatt atctggatgg caaaccggtg | 1680 |
| agcgcgaccg tgcgcgcgct gattgaaaaa ctgctggcgc agtatggcgg c | 1731 |

<210> SEQ ID NO 2
<211> LENGTH: 1911
<212> TYPE: DNA
<213> ORGANISM: Artificial Sequence
<220> FEATURE:
<223> OTHER INFORMATION: the sequence is synthetized

<400> SEQUENCE: 2

```
aaactgacca ccaccaccct ggcgctggcg accggcgcgg cggcggcgga agcgagctat      60
catctggata ccaccgcgcc gccgccgacc aacctgagca ccctgccgaa caacaccctg     120
tttcatgtgt ggcgcccgcg cgcgcatatt ctgccggcgg aaggccagat tggcgatccg     180
tgcgcgcatt ataccgatcc gagcaccggc ctgtttcatg tgggcttcct gcatgatggc     240
gatggcattg cgggcgcgac caccgcgaac ctggcgacct ataccgatac cagcgataac     300
tttctgattc agccgggcgg caaaaacgat ccggtggcgg tgtttgatgg cgcggtgatt     360
ccggtgggcg tgaacaacac cccgaccctg ctgtataccg gcgtgagctt tctgccgatt     420
tggagcattc cgtataccg cggcagcgaa acccagagcc tggcggtggc gcgcgatggc     480
ggccgccgct tgataaact ggatcagggc ccggtgattg cggatcatcc gtttgcggtg     540
gatgtgaccg cgtttcgcga tccgtttgtg tttcgcagcg cgaaactgga tgtgctgctg     600
gatgaagaag tggcgcgcaa cgaaaccgcg gtgcagcagg cggtggatgg ctggaccgaa     660
aaaaacgcgc cgtggtatgt ggcggtgagc ggcggcgtgc atggcgtggg cccggcgcag     720
tttctgtatc gccagaacgg cggcaacgcg agcgaatttc agtattggga atatctgggc     780
gaatggtgga aggaagcgac caacagcagc tggggcgatg aaggcacctg gcgggccgc     840 tggggctttta actttgaaac cggcaacgtg ctgtttctga ccgaagaagg ccatgatccg     900
cagaccggcg aagtgtttgt gaccctgggc accgaaggca cgggcctgcc gccgcaggtg     960
agcagcattc atgatatgct gtgggcggcg ggcgaagtgg gcgtgggcag cgaacaggaa    1020
aaagtggaat ttagcccgag catggcgggc tttctggatt ggggctttag cgcgtatgcg    1080
gcggcgggca aagtgctgcc ggcgagcagc gcggtgagca aaaccagcgg cgtggaagtg    1140
gatcgctatg tgagctttgt gtggctgacc ggcgatcagt atgaacaggc ggatggcttt    1200
ccgaccgcgc agcagggctg gggcagcctg ctgctgccgc gcgaactgaa aaccgtggaa    1260
aacgtggtgg ataacgaact ggtgcgcgaa gaaggcgtga gctgggtggt gggcgaaagc    1320
gataaccaga ccgcgcgcct gcgcacccctg ggcattacca ttgcgcgcga aaccaaagcg    1380
gcgctgctgg cgaacggcag cgtgaccgcg aagaagatc gcaccctgca gaccgcggcg    1440
gtggtgccgt ttgcgcagag cccgagcagc aaatttttg tgctgaccgc gcagctggat    1500
gcgagcgcgc gcagcagccc gctgcagagc ggctttgaaa ttctggcgag cgaactggaa    1560
cgcaccgcga tttattatca gtttagcaac gaaagcctgg tggtggatcg cagccagacc    1620
agcgcggcgg cgccgaccaa cccggatagc tttaccgaaa gcggcaaact gcgcctgttt    1680
gatgtgattg aaaacggcca ggaacaggtg aaaccctgg atctgaccgt ggtggtggat    1740
aacgcggtgg tggaagtgta tgcgaacggc cgctttgcgc tgagcacctg ggcgcgcagc    1800
tggtatgata cagcaccca gattcgcttt tttcataacg gcgaaggcga agtgcagttt    1860
cgcaacgtga gcgtgagcga aggcctgtat aacgcgtggc cggaacgcaa c            1911
```

<210> SEQ ID NO 3
<211> LENGTH: 577
<212> TYPE: PRT
<213> ORGANISM: Microbacterium saccharophilum

<400> SEQUENCE: 3

```
Thr His Ser Thr Arg Gly Arg Val Arg Arg Val Leu Ala Gly Gly Leu
1               5                   10                  15

Ala Thr Ser Thr Leu Ala Ala Ala Val Leu Ile Ala Gly Ala Ala Pro
            20                  25                  30
```

```
Ala Thr Ala Gln Ser Gly Leu Gln Asp Gly Pro Glu Pro Thr Ile His
             35                  40                  45
Thr Gln Gln Ala Tyr Ala Pro Glu Asp Phe Thr Ala Lys Trp Thr
 50                  55                  60
Arg Ala Asp Ala Arg Gln Leu Gln Arg Met Ser Asp Pro Thr Ala Pro
 65                  70                  75                  80
Ser Arg Glu Asn Ser Met Pro Ala Ser Val Thr Met Pro Thr Val Pro
                 85                  90                  95
Gln Asp Phe Pro Asp Met Ser Asn Glu Gln Val Trp Val Trp Asp Thr
             100                 105                 110
Trp Pro Leu Thr Asp Glu Asp Ala Asn Gln Tyr Ser Val Asn Gly Trp
             115                 120                 125
Glu Ile Ile Phe Ser Leu Val Ala Asp Arg Asn Leu Gly Phe Asp Asp
             130                 135                 140
Arg His Val Phe Ala Lys Ile Gly Tyr Phe Tyr Arg Pro Ala Gly Val
145                 150                 155                 160
Pro Ala Ala Glu Arg Pro Glu Asn Gly Gly Trp Thr Tyr Gly Gly Leu
                 165                 170                 175
Val Phe Lys Glu Gly Val Thr Gly Gln Ile Phe Glu Asp Gln Ser Phe
             180                 185                 190
Ser His Gln Thr Gln Trp Ser Gly Ser Ala Arg Val Ser Lys Asn Gly
             195                 200                 205
Glu Ile Lys Leu Phe Phe Thr Asp Val Ala Phe Tyr Arg Asn Ser Asp
             210                 215                 220
Gly Thr Asn Ile Lys Pro Tyr Asp Pro Arg Ile Ala Leu Ser Val Gly
225                 230                 235                 240
Lys Val Lys Ala Asn Lys Lys Gly Val Thr Leu Thr Gly Phe Asn Lys
                 245                 250                 255
Val Thr Asp Leu Leu Gln Ala Asp Gly Thr Tyr Tyr Gln Thr Gly Ala
             260                 265                 270
Gln Asn Glu Phe Phe Asn Phe Arg Asp Pro Phe Thr Phe Glu Asp Pro
             275                 280                 285
Ala His Pro Gly Glu Thr Phe Met Val Phe Glu Gly Asn Ser Ala Met
             290                 295                 300
Gln Arg Glu Thr Ala Thr Cys Asn Glu Ala Asp Leu Gly Tyr Arg Gln
305                 310                 315                 320
Gly Asp Pro Tyr Ala Glu Thr Val Asp Val Asn Ala Ser Gly Ala
                 325                 330                 335
Thr Tyr Gln Ile Gly Asn Val Gly Leu Ala Lys Ala Lys Asn Lys Gln
             340                 345                 350
Leu Thr Glu Trp Glu Phe Leu Pro Pro Ile Leu Ser Ala Asn Cys Val
             355                 360                 365
Thr Asp Gln Thr Glu Arg Pro Gln Ile Tyr Phe Lys Asp Gly Lys Ser
 370                 375                 380
Tyr Leu Phe Thr Ile Ser His Arg Gly Thr Phe Ala Ala Gly Leu Asp
385                 390                 395                 400
Gly Pro Glu Gly Val Tyr Gly Phe Val Gly Asp Gly Ile Arg Ser Asp
                 405                 410                 415
Tyr Gln Pro Leu Asn Gly Gly Ser Gly Leu Ala Leu Gly Asn Pro Thr
             420                 425                 430
Asn Leu Asn Phe Leu Gly Gly Gln Pro Phe Ala Pro Asp Phe Asn Gln
             435                 440                 445
His Pro Gly His Phe Gln Ala Tyr Ser His Tyr Val Met Pro Gly Gly
```

```
                450             455             460
Leu Val Gln Ser Phe Ile Asp Thr Ile Gly Thr His Asp Asp Phe Val
465                 470             475                 480

Arg Gly Gly Thr Leu Ala Pro Thr Val Lys Met Asp Ile Gly Val Gly
                485             490                 495

Gly Asp Pro Thr Lys Thr Ala Val Asp Tyr Ser Tyr Gly Ser Glu Gly
            500             505             510

Leu Gly Gly Trp Ala Asp Ile Pro Ala Asn Lys His Leu Phe Thr Asn
        515             520             525

Gly Lys Phe Gly Val Ala Val Ser Asp Glu Ala Ala Gln Lys Ile Arg
    530             535             540

Lys Ile Leu Gly Ser Lys Phe Asp Asp Tyr Leu Asp Gly Lys Pro Val
545             550             555                 560

Ser Ala Thr Val Arg Ala Leu Ile Glu Lys Leu Leu Ala Gln Tyr Gly
                565             570             575

Gly

<210> SEQ ID NO 4
<211> LENGTH: 637
<212> TYPE: PRT
<213> ORGANISM: Aspergillus japonicus

<400> SEQUENCE: 4

Lys Leu Thr Thr Thr Thr Leu Ala Leu Ala Thr Gly Ala Ala Ala Ala
1               5                   10                  15

Glu Ala Ser Tyr His Leu Asp Thr Thr Ala Pro Pro Thr Asn Leu
            20                  25                  30

Ser Thr Leu Pro Asn Asn Thr Leu Phe His Val Trp Arg Pro Arg Ala
        35                  40                  45

His Ile Leu Pro Ala Glu Gly Gln Ile Gly Asp Pro Cys Ala His Tyr
    50                  55                  60

Thr Asp Pro Ser Thr Gly Leu Phe His Val Gly Phe Leu His Asp Gly
65                  70                  75                  80

Asp Gly Ile Ala Gly Ala Thr Thr Ala Asn Leu Ala Thr Tyr Thr Asp
                85                  90                  95

Thr Ser Asp Asn Phe Leu Ile Gln Pro Gly Gly Lys Asn Asp Pro Val
            100                 105                 110

Ala Val Phe Asp Gly Ala Val Ile Pro Val Gly Val Asn Asn Thr Pro
        115                 120                 125

Thr Leu Leu Tyr Thr Ser Val Ser Phe Leu Pro Ile Trp Ser Ile Pro
    130                 135                 140

Tyr Thr Arg Gly Ser Glu Thr Gln Ser Leu Ala Val Ala Arg Asp Gly
145                 150                 155                 160

Gly Arg Arg Phe Asp Lys Leu Asp Gln Gly Pro Val Ile Ala Asp His
                165                 170                 175

Pro Phe Ala Val Asp Val Thr Ala Phe Arg Asp Pro Phe Val Phe Arg
            180                 185                 190

Ser Ala Lys Leu Asp Val Leu Leu Asp Glu Glu Val Ala Arg Asn Glu
        195                 200                 205

Thr Ala Val Gln Gln Ala Val Asp Gly Trp Thr Glu Lys Asn Ala Pro
    210                 215                 220

Trp Tyr Val Ala Val Ser Gly Val His Gly Val Gly Pro Ala Gln
225                 230                 235                 240

Phe Leu Tyr Arg Gln Asn Gly Gly Asn Ala Ser Glu Phe Gln Tyr Trp
```

245                 250                 255
Glu Tyr Leu Gly Glu Trp Trp Gln Glu Ala Thr Asn Ser Ser Trp Gly
            260                 265                 270

Asp Glu Gly Thr Trp Ala Gly Arg Trp Gly Phe Asn Phe Glu Thr Gly
            275                 280                 285

Asn Val Leu Phe Leu Thr Glu Gly His Asp Pro Gln Thr Gly Glu
        290                 295                 300

Val Phe Val Thr Leu Gly Thr Glu Gly Ser Gly Leu Pro Pro Gln Val
305                 310                 315                 320

Ser Ser Ile His Asp Met Leu Trp Ala Ala Gly Glu Val Gly Val Gly
            325                 330                 335

Ser Glu Gln Glu Lys Val Glu Phe Ser Pro Ser Met Ala Gly Phe Leu
            340                 345                 350

Asp Trp Gly Phe Ser Ala Tyr Ala Ala Gly Lys Val Leu Pro Ala
            355                 360                 365

Ser Ser Ala Val Ser Lys Thr Ser Gly Val Glu Val Asp Arg Tyr Val
        370                 375                 380

Ser Phe Val Trp Leu Thr Gly Asp Gln Tyr Glu Gln Ala Asp Gly Phe
385                 390                 395                 400

Pro Thr Ala Gln Gln Gly Trp Gly Ser Leu Leu Pro Arg Glu Leu
            405                 410                 415

Lys Thr Val Glu Asn Val Val Asp Asn Glu Leu Val Arg Glu Gly
            420                 425                 430

Val Ser Trp Val Val Gly Glu Ser Asp Asn Gln Thr Ala Arg Leu Arg
            435                 440                 445

Thr Leu Gly Ile Thr Ile Ala Arg Glu Thr Lys Ala Ala Leu Leu Ala
        450                 455                 460

Asn Gly Ser Val Thr Ala Glu Glu Asp Arg Thr Leu Gln Thr Ala Ala
465                 470                 475                 480

Val Val Pro Phe Ala Gln Ser Pro Ser Ser Lys Phe Phe Val Leu Thr
            485                 490                 495

Ala Gln Leu Asp Ala Ser Ala Arg Ser Ser Pro Leu Gln Ser Gly Phe
            500                 505                 510

Glu Ile Leu Ala Ser Glu Leu Glu Arg Thr Ala Ile Tyr Tyr Gln Phe
        515                 520                 525

Ser Asn Glu Ser Leu Val Val Asp Arg Ser Gln Thr Ser Ala Ala Ala
        530                 535                 540

Pro Thr Asn Pro Asp Ser Phe Thr Glu Ser Gly Lys Leu Arg Leu Phe
545                 550                 555                 560

Asp Val Ile Glu Asn Gly Gln Glu Gln Val Glu Thr Leu Asp Leu Thr
            565                 570                 575

Val Val Val Asp Asn Ala Val Val Glu Val Tyr Ala Asn Gly Arg Phe
            580                 585                 590

Ala Leu Ser Thr Trp Ala Arg Ser Trp Tyr Asp Asn Ser Thr Gln Ile
            595                 600                 605

Arg Phe Phe His Asn Gly Glu Gly Glu Val Gln Phe Arg Asn Val Ser
        610                 615                 620

Val Ser Glu Gly Leu Tyr Asn Ala Trp Pro Glu Arg Asn
625                 630                 635

<210> SEQ ID NO 5
<211> LENGTH: 29
<212> TYPE: DNA
<213> ORGANISM: Artificial Sequence

```
<220> FEATURE:
<223> OTHER INFORMATION: the sequence is synthetized

<400> SEQUENCE: 5
cgcggatcca tgacccatag cacccgcgg                                29

<210> SEQ ID NO 6
<211> LENGTH: 29
<212> TYPE: DNA
<213> ORGANISM: Artificial Sequence
<220> FEATURE:
<223> OTHER INFORMATION: the sequence is synthetized

<400> SEQUENCE: 6
cccaagcttc ggcggtatga cgcggtcgt                                29

<210> SEQ ID NO 7
<211> LENGTH: 30
<212> TYPE: DNA
<213> ORGANISM: Artificial Sequence
<220> FEATURE:
<223> OTHER INFORMATION: the sequence is synthetized

<400> SEQUENCE: 7
cgcggatcca tgaaactgac caccaccacc                               30

<210> SEQ ID NO 8
<211> LENGTH: 31
<212> TYPE: DNA
<213> ORGANISM: Artificial Sequence
<220> FEATURE:
<223> OTHER INFORMATION: the sequence is synthetized

<400> SEQUENCE: 8
cccaagcttc aacgcaaggc cggtgcgcaa t                             31
```